(12) United States Patent
Roth

(10) Patent No.: US 8,092,499 B1
(45) Date of Patent: Jan. 10, 2012

(54) SKELETAL FLEXIBLE/RIGID ROD FOR TREATING SKELETAL CURVATURE

(76) Inventor: Herbert J. Roth, Bloomfield, MI (US)

(*) Notice: Subject to any disclaimer, the term of this patent is extended or adjusted under 35 U.S.C. 154(b) by 435 days.

(21) Appl. No.: 12/008,566

(22) Filed: Jan. 11, 2008

(51) Int. Cl.
*A61B 17/70* (2006.01)
*A61B 17/88* (2006.01)
(52) U.S. Cl. ......... 606/254; 606/258; 606/259; 606/279
(58) Field of Classification Search .......... 606/246–279; A61B 17/70
See application file for complete search history.

(56) References Cited

U.S. PATENT DOCUMENTS

| | | | |
|---|---|---|---|
| 2,438,434 A * | 3/1948 | Friedman | 220/8 |
| 3,967,525 A * | 7/1976 | Lerich | 411/69 |
| 4,719,912 A * | 1/1988 | Bonomo et al. | 606/192 |
| 4,919,133 A * | 4/1990 | Chiang | 606/159 |
| 5,350,379 A * | 9/1994 | Spievack | 606/63 |
| 5,626,579 A * | 5/1997 | Muschler et al. | 606/60 |
| 5,720,746 A * | 2/1998 | Soubeiran | 606/62 |
| 6,623,484 B2 | 9/2003 | Betz et al. | |
| 6,755,862 B2 * | 6/2004 | Keynan | 623/16.11 |
| 6,796,984 B2 * | 9/2004 | Soubeiran | 606/300 |
| 6,989,011 B2 | 1/2006 | Paul et al. | |
| 7,128,147 B2 * | 10/2006 | Marcin et al. | 166/208 |
| 7,137,985 B2 | 11/2006 | Jahng | |
| 2003/0080870 A1 * | 5/2003 | Marmaropoulos et al. | 340/573.1 |
| 2005/0038432 A1 | 2/2005 | Shaolian et al. | |
| 2005/0113927 A1 | 5/2005 | Malek | |
| 2005/0131407 A1 | 6/2005 | Sicvol et al. | |
| 2006/0009767 A1 * | 1/2006 | Kiester | 606/61 |
| 2006/0047282 A1 | 3/2006 | Gordon | |
| 2006/0079897 A1 | 4/2006 | Harrison et al. | |
| 2006/0084984 A1 * | 4/2006 | Kim | 606/61 |
| 2006/0250203 A1 * | 11/2006 | Marmaropoulos et al. | 335/205 |
| 2007/0093813 A1 | 4/2007 | Calahan et al. | |
| 2007/0118122 A1 | 5/2007 | Butler et al. | |
| 2007/0233098 A1 | 10/2007 | Mastrorio et al. | |
| 2007/0293862 A1 * | 12/2007 | Jackson | 606/61 |
| 2009/0306717 A1 * | 12/2009 | Kercher et al. | 606/258 |

FOREIGN PATENT DOCUMENTS

FR 2738144 A1 3/1997

OTHER PUBLICATIONS

Irving Skeist, Handbook of Adhesives, Second Edition, 1977, Chapter 53, pp. 818-835, Litton Educational Publishing, Inc.
Barry Arkles, Look What You Can Make Out of Silicones, Chemtech, 1983, pp. 542-555.
Silastic MDX 4-4210 BioMedical Grade Elastomer, Dow Corning, 2007.

* cited by examiner

*Primary Examiner* — Eduardo C Robert
*Assistant Examiner* — Nicholas Plionis
(74) *Attorney, Agent, or Firm* — Quinn Law Group, PLLC

(57) ABSTRACT

An apparatus for treatment of a body having a skeletal curvature comprising:
a rod capable of being attached to at least two vertebrae of the spine; which rod, under fluid pressure moves from a first position to an extended position, which extended position straightens the two vertebrae; and
a hydraulic mechanism, in fluid communication with the rod, which moves the rod from the first position to the extended position, wherein the rod and hydraulic mechanism are capable of being inserted within the body having a skeletal curvature.

26 Claims, 6 Drawing Sheets

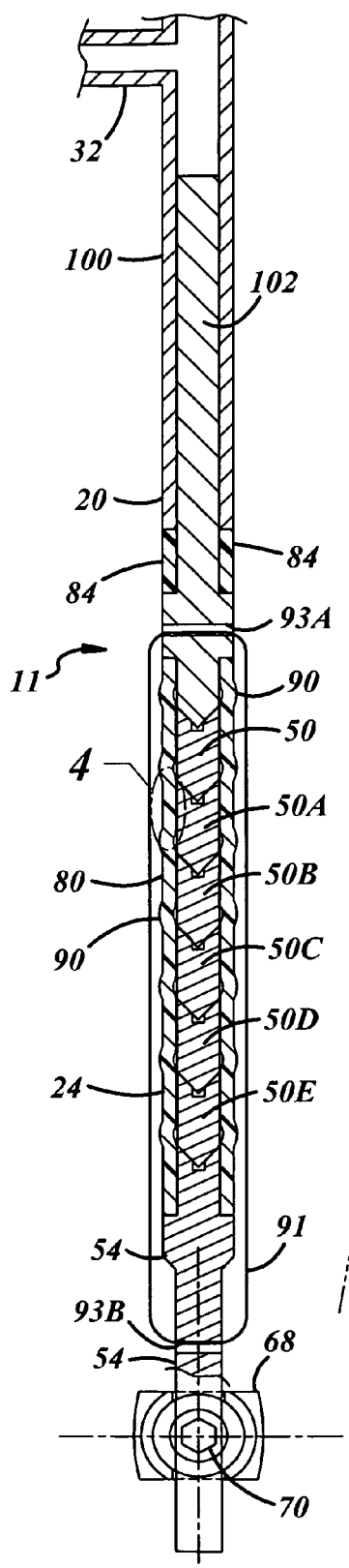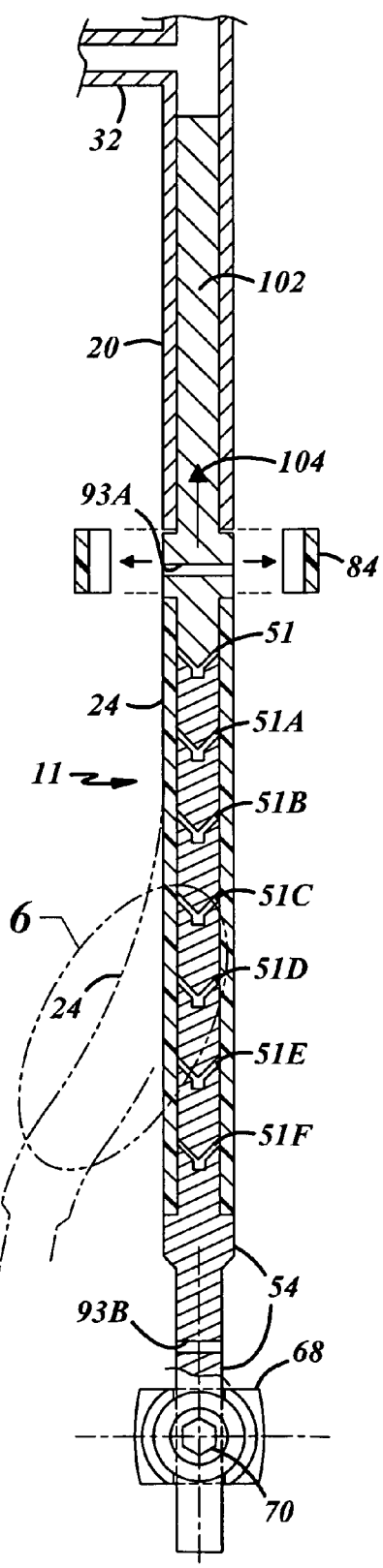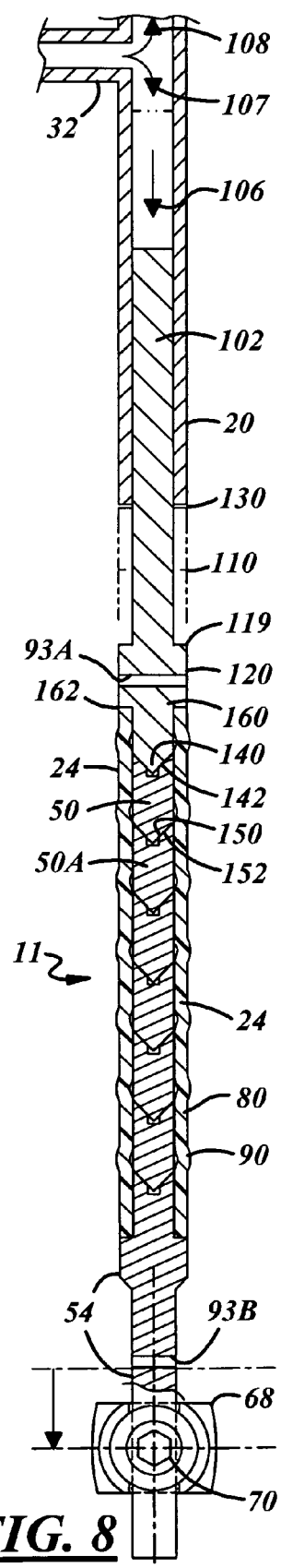
*FIG. 3*   *FIG. 5*   *FIG. 8*

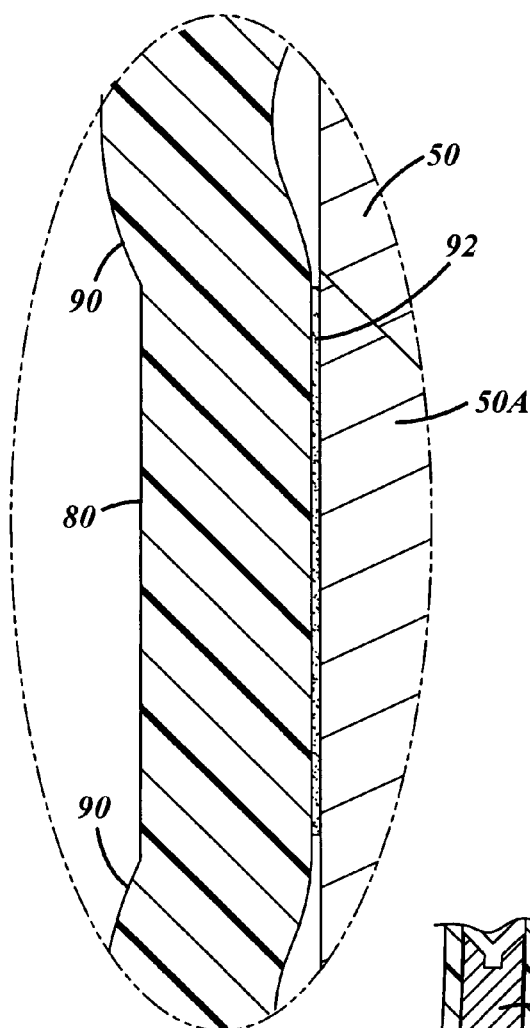
*FIG. 4*
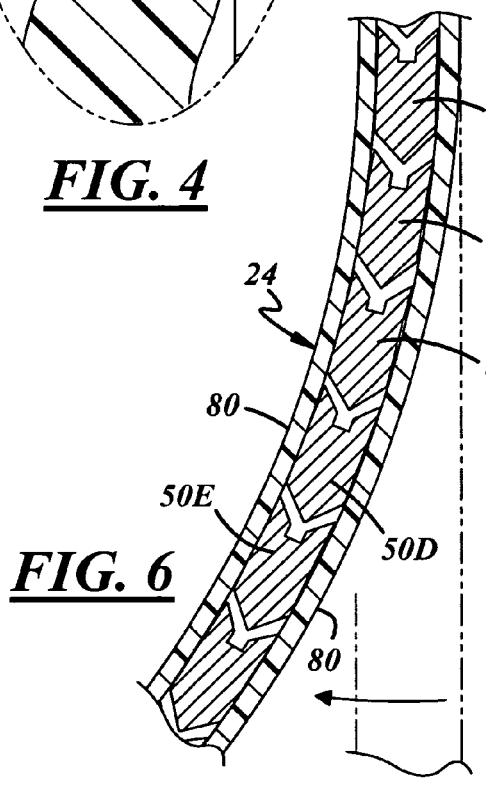
*FIG. 6*
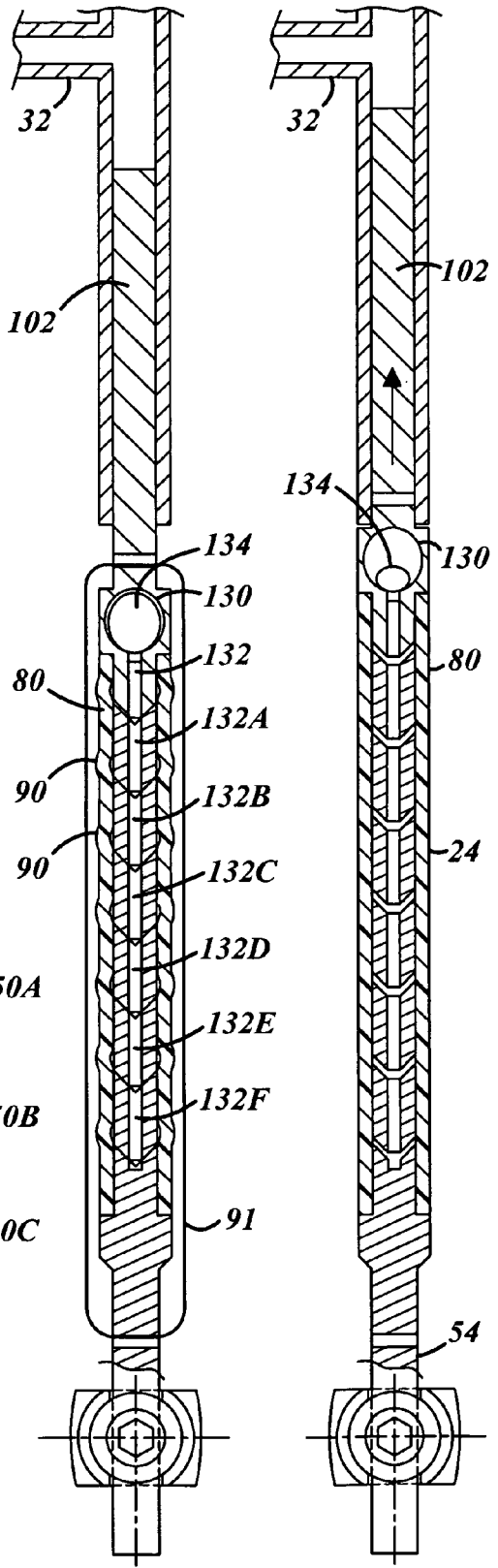
*FIG. 10*   *FIG. 11*

SKELETAL FLEXIBLE/RIGID ROD FOR TREATING SKELETAL CURVATURE

FIELD OF THE INVENTION

The present invention pertains to the field of treating skeletal curvature of a body utilizing instruments that can be inserted into the body and stabilize the spine. In particular, the invention is concerned with utilizing an outer garment that can activate the instruments inserted in the human body.

BACKGROUND OF THE INVENTION

United States Publication 2007/0093, 813 discloses a dynamic spinal stabilizer. FIG. 4 shows a rigid rod 18 made up of members 24 that have male and female connecting segments. There is a space between the members 24 to go from a flexible to a rigid position. See FIG. 5. In a similar fashion, see United States publication 2005/0131,417. Note in FIG. 1 that there is rod 30 on which members 12 A-F are inserted. These are flexible but rigid, when the members are joined together. Note however that they are connected by cable 30. Also in a similar fashion, see U.S. Pat. No. 7,137, 985, in particular FIGS. 12 A-C. Members 37 likewise are held together by flexible wire 32.Other flexible systems are described in U.S. Pat. No. 6,989,011.

United States publication, 2006/0079,897 describes an apparatus for incrementally manipulating a body member. A magnetic implant adapted to be received on a location of the body member and a form external to the patient make up the apparatus. The magnetic member generates a magnetic force between the implant and the external form to incrementally manipulate the member. The front page of the patent shows the external form, which is wrapped around the patient so that it can be positioned with the magnet, located within the patient. A mechanical jackscrew is described in FIG. 25. Paragraph 206 on page 13 indicates that the form may be worn by the patient at night.

United States publication 2006/0009,767 discloses an implantable rod, which is under external incremental force. The expandable rod, as shown in FIG. 2 a, is activated by electromagnetic radiation. The motor causes the rod to rotate and expand in only one direction.

Other references that may be of interest, but not necessarily prior art to this application, are as follows:

U.S. Pat. No. 7,137,985, U.S. Pat. No. 6,989,011, U.S. Pat. No. 6,623,484, United States Patent Publication 2007/ 0093813, United States Patent Publication 2007/0118122, United States Patent Publication 2007/0233098, United States Patent Publication 2006/0009767, United States Patent Publication 2006/0047282, United States Patent Publication 2006/0079897, United States Patent Publication 2005/ 0113927, United States Patent Publication 2005/0038432, United States Patent Publication and United States Patent Publication 2005/0131407
The following foreign patent may also be of interest:
FR 2738144.

There is a need to have instruments that can assist in treating or stabilizing curvature of the spine or for correcting spine deformities that can be adaptable to the stresses of day to day living by the patient yet at the same time achieve stabilization of the spine.

There is a need to have instruments that can assist in treating or stabilizing curvature of the spine or for correcting spine deformities that can be adaptable to the individual needs of a patient, yet at the same time achieve stabilization of the spine.

There is a need to have flexible instruments that can be inserted into a patient having a need for treating or stabilizing curvature of the spine or for correcting spine deformities and adaptable to the patient's needs.

There is a need to facilitate straightening the curvature of the spine without fusing the vertebrae.

SUMMARY OF THE INVENTION

Described is an apparatus for treatment of a body having a skeletal curvature comprising: a rod capable of being attached to at least two vertebrae of the spine; which rod under fluid pressure moves from a first position to an extended position, which extended position straightens the two vertebrae; and a hydraulic mechanism, in fluid communication with the rod, which moves the rod from the first position to the extended position, wherein the rod and hydraulic mechanism are capable of being inserted within the body having a skeletal curvature.

Also described is a method of moving vertebrae in a spine having a curvature comprising providing the apparatus described above; and causing the fluid to move in the hydraulic mechanism thereby moving the vertebrae.

Also described is a flexible rod capable of being attached to vertebrae of the spine comprising a first end capable of being attached to one vertebrae and a second end, separated from the first end and capable of attaching to a separate second vertebrae, which rod, under fluid pressure moves from a first position to an extended position, which extended position straightens the vertebrae; and a chamber, located between the ends, and within which chamber is located a plurality of cones; under fluid pressure the cones engage each other to make the rod less flexible in the extended position.

Also described is a method of moving vertebrae in a spine having a curvature comprising providing the apparatus described immediately above; and causing the fluid to move in the chamber to move the cones, thereby moving the vertebrae.

Also described is an apparatus for treatment of a body having a skeletal curvature comprising: a rod capable of being attached to at least two vertebrae of the spine; which rod, under fluid pressure moves from a first position to an extended position, which extended position straightens the two vertebrae; and
a hydraulic mechanism, in fluid communication with the rod, which moves the rod from the first position to the extended position, wherein the rod and hydraulic mechanism are capable of being inserted within the body having a skeletal curvature,
further comprising a garment, capable of being worn external to the body in which the rod and hydraulic mechanism are inserted, wherein the garment comprises an activating mechanism to cause the hydraulic mechanism to move the rod from the first position to the extended position, wherein the rod further comprises a fixed central element and a segment, attached thereto, capable of being extended from an initial position to an extended position, which segment capable of being extended is comprised of an elastomeric material and further comprises a chamber in which there is a plurality of metallic cones capable of fitting one juxtaposed to the other thereby extending the rod. Also described is a method of moving vertebrae in a spine having a curvature comprising providing the apparatus immediately described above; and causing the fluid to move in the hydraulic mechanism thereby moving the vertebrae.

BRIEF DESCRIPTION OF THE DRAWINGS

These and other objects, features and advantages of this invention will be apparent from the following detailed description, appended claims and accompanied drawings in which:

FIG. 3 is a partial sectional schematic representation of the rod of the present invention taken the long lines 3-3 of FIG. 2, when inserted into the body;

FIG. 4 is an exploded version of a schematic representation of FIG. 3 of a portion of the rod of the present invention;

FIG. 5 is a partial sectional schematic representation of the rod of the present invention, showing the alignment in a flexible position;

FIG. 6 is a partial sectional schematic representation of a portion of the rod of the present invention in the flexible position;

FIG. 8 is a partial sectional schematic representation of the rod of the present invention after it is inserted into the body in the rigid/extended position;

FIG. 10 is a partial sectional representation of the rod of the present invention in an alternative embodiment in an extended position;

FIG. 11 is a partial, sectional representation of an alternative embodiment of the rod of the present invention, prior to moving to an extended position;

DETAILED DESCRIPTION OF THE INVENTION

Definitions

By cone is meant a member that assists in making the elastomeric portion of the rod more or less flexible, depending on the fluid pressure exerted on the cone to extend the rod.

By curvature of the spine or skeletal curvature is meant to include scoliosis or other comparable clinical conditions.

By fluid is meant a liquid, such as saline, or a gas, such as an oxygen containing gas, such as air.

By inert is meant that the metal or plastic material described herein is stable within the body cavity.

By saline is meant an aqueous solution generally containing sodium chloride and other materials stable in the human body.

By straighten is meant to attempt to reduce the curvature of the spine.

In general, the rod of the present invention is utilized as follows.

Figure 7:
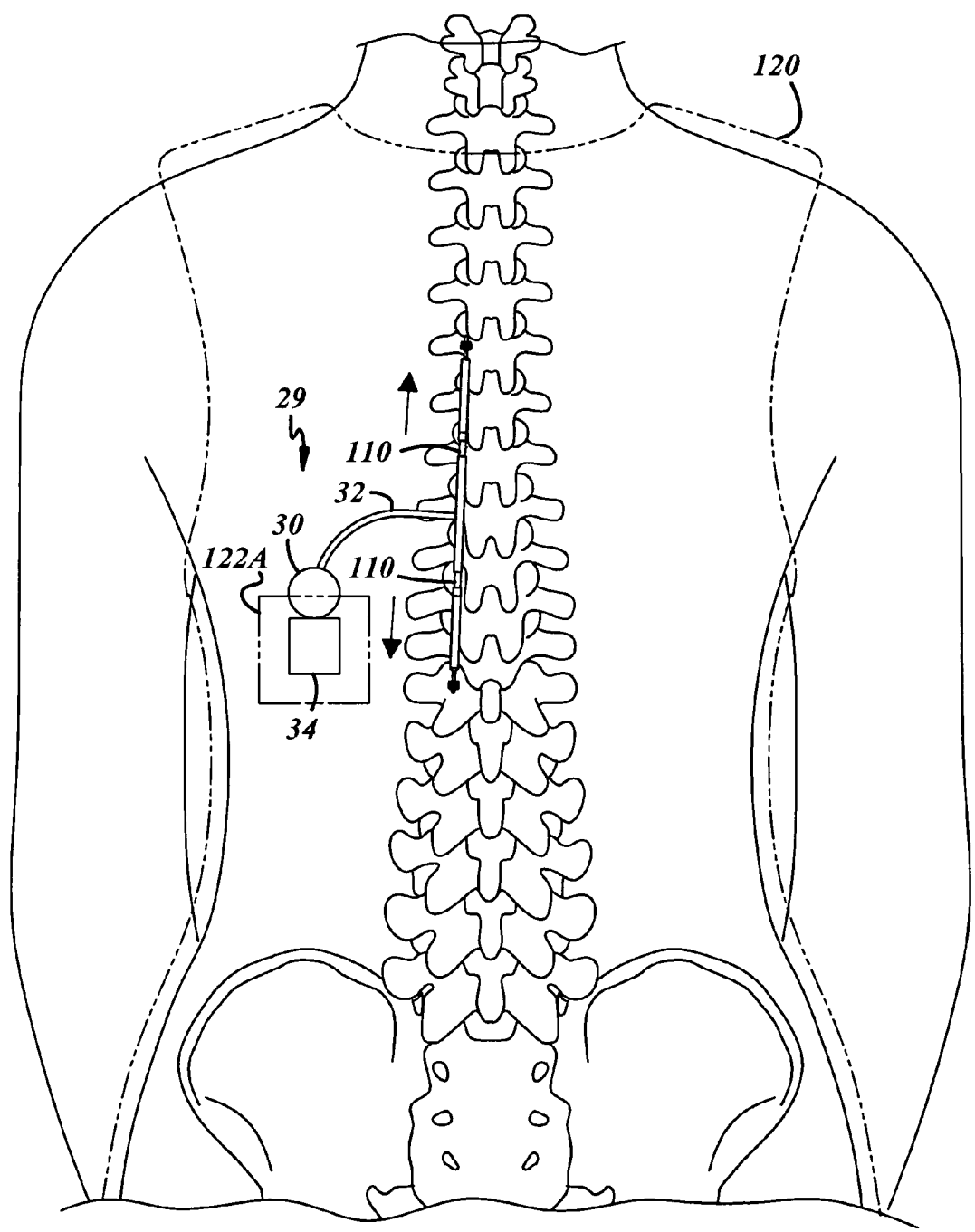
FIG. 7 is a schematic representation of the rod of the present invention in an extended position on the spine which is in a straightened position with the over garment in alignment with the rod of the present invention.
Figures 9, 12:
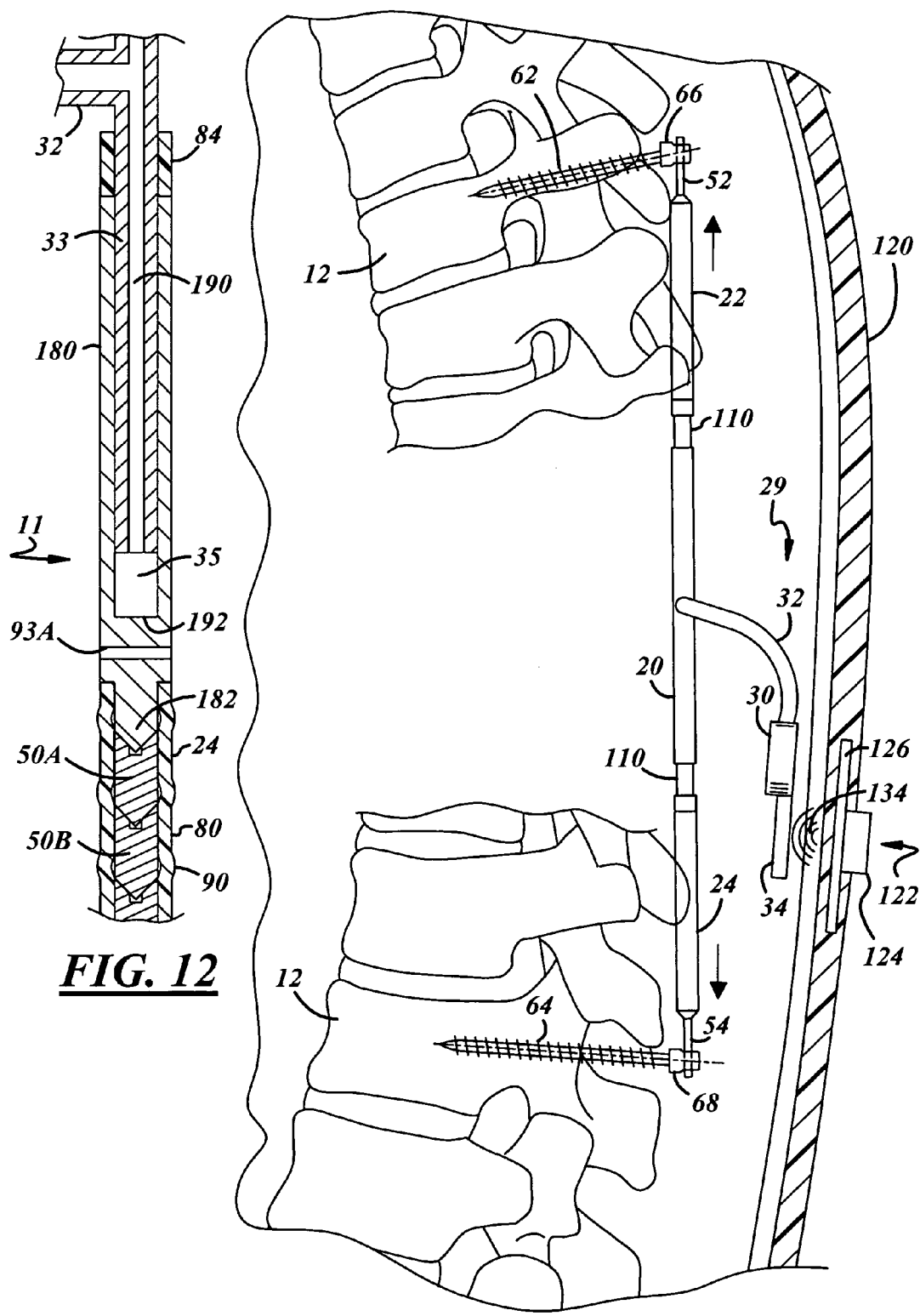
FIG. 9 is a partial sectional schematic representation of the rod of the present invention with the over garment aligned with the rod of the present invention.
FIG. 12 is a partial, sectional representation of an alternative embodiment of the rod of the present invention.

In a human patient with a curvature of the spine, as represented schematically in figure number 1, the rod is screwed onto a patient's spine in an extended position. In order to move the spine from the curved position of FIG. 1 to a straightened position in FIG. 7, the rod is moved to an extended position. The extension occurs by movement of a fluid against metallic members inside the rod, which facilitate an extension of the rod. The amount of extension attained depends upon the amount of curvature that one desires to be corrected in the time frame allotted for treatment. Activation of the fluid within the rod occurs by the patient wearing a garment as shown in FIG. 7 where an activating mechanism as shown in FIG. 9 causes the rod to be extended. The garment acts as a support for the spine to keep it in a straightened condition and at the same time, facilitating the rod to be in an extended position without undue pressure on it which could damage it. If the garment were not used, the rod may be damaged in the body by movement of the patient. When the garment is removed, the rod reverts to a flexible position, thereby facilitating day to day activities of the patient. While it is anticipated the garment would be used in the evening while a patient sleeps, it is to be appreciated that it may be used at other times to facilitate treatment of the spine curvature.

It is also desirable that the patient, by utilization of the invention described herein, will not need to have the vertebrae fused.

Figure 1:
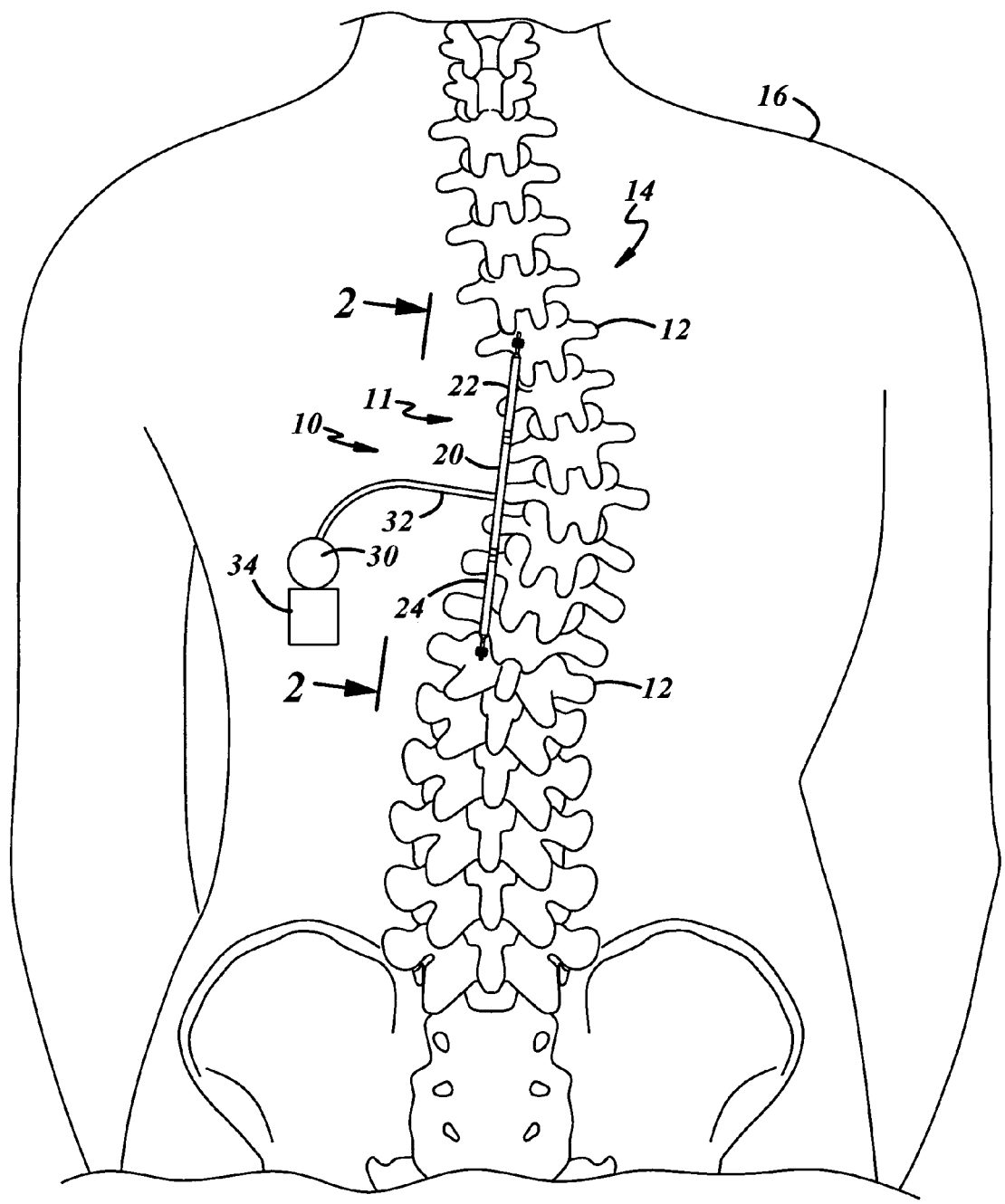
FIG. 1 is a schematic representation of a human spine with a curvature and the installation of the invention on the spine.

Further, when the rod is removed after treatment, the back and vertebrae will be flexible. This is to be contrasted with vertebrae that are fused as part of other treatment processes. Turning now to the drawings in the case:

FIG. 1 shows the rod assembly 10 of the present invention comprised of a rod 11 screwed into two spaced apart vertebrae 12 of the spine 14 present in the body 16. The rod 11 has a fixed, generally solid central element 20 with two segments 22 and 24 capable of being extended, thereby causing the curvature of the spine to become straightened as shown in FIG. 7. FIG. 1 also schematically shows that the rod 11 of the present invention is connected to a source of fluid 30 by conduit 32. The fluid can be activated in source 30 by activating mechanism 34, such as, a pump, and the like.

Figure 2:
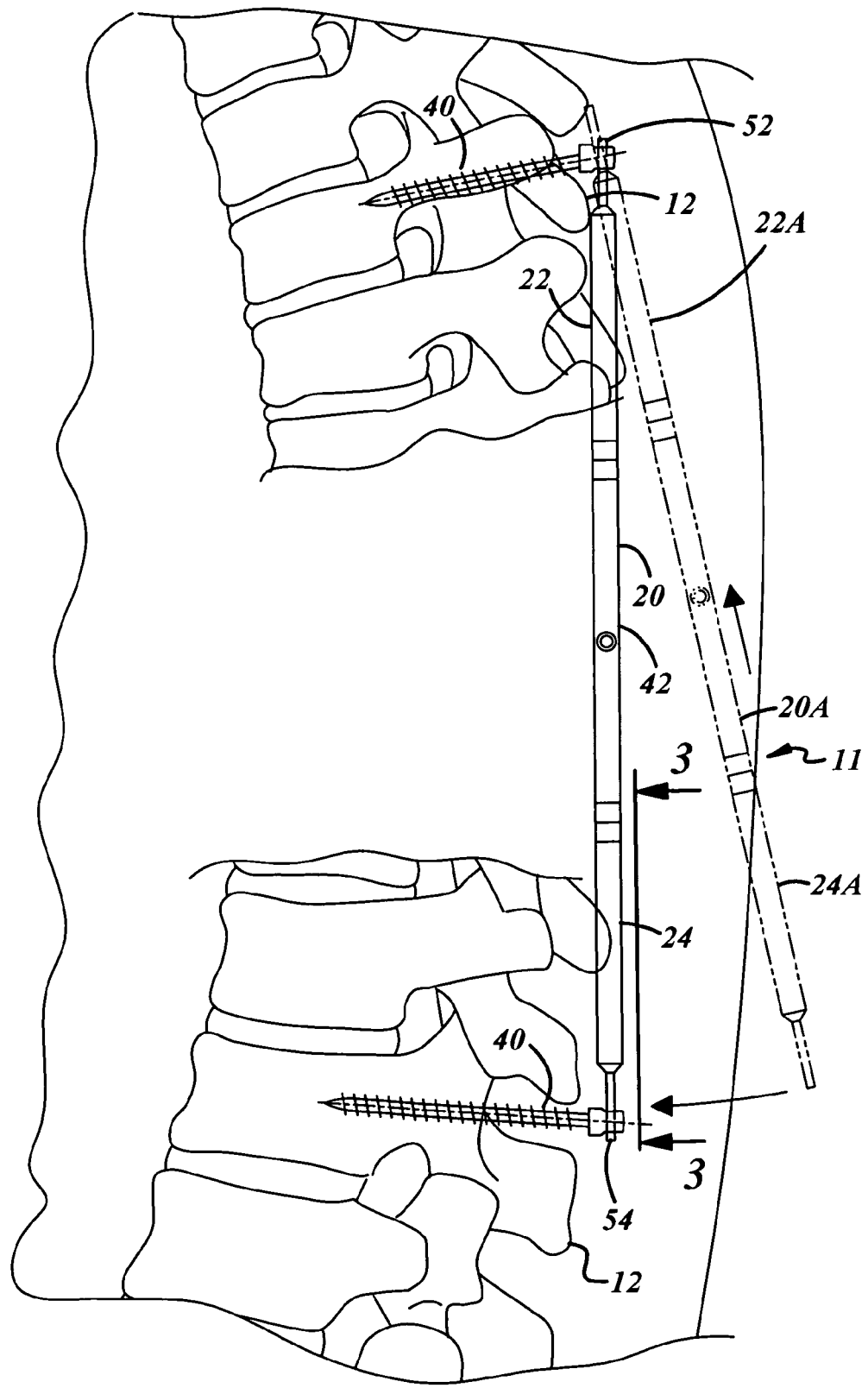
FIG. 2 is a further partial schematic representation of the invention taken the long lines 2-2 of FIG. 1.

While applicant does not wish to be bound to any particular theory, it is believed advantageous that the rod should be inserted into the body in an extended condition, as shown in FIGS. 2 and 3. The rod 11, in outline form, 20 A, 22 A and 24 A, is inserted from outside the body to inside the body. As shown in FIG. 2, the rod 11, with its component parts, central element 20, and extended portions 22 and 24, is attached to the spine by pedicle screws 40. The conduit 32 fits into opening 42 in the central fixed element for movement of the fluid into the central fixed element 20.

FIG. 3 is a partial sectional schematic representation of the rod 11 after it is inserted into the body. The rod has central portion 20 with conduit 32 and extendable portion 24. The central portion 20 can be comprised of a variety of stable materials such as inert metals or plastics such as, titanium, stainless steel and the like or other inert plastics such as thermoset or thermoplastic materials and the like.

Within the extended portion 24 is a metallic structure 50, which preferably may be comprised of a plurality of metallic cones 50 A-50 E. The number of cones 50-50 E needed for achieving extension can vary with desired extension for a particular curvature of the spine. The ends 52 and 54 of the extendable elements 22 and 24, best shown in FIG. 9, have apertures (not shown) in which the pedicle screw components (threaded elements 62 and 64; caps 66 and 68 with hexagonal locking screw 70) are attached. The ends 52 and 54 likewise are comprised of a metallic material such as titanium or stainless steel and the like. The metallic members 50-50 E and 54 are fixedly attached by element 92 (FIG. 4) to the elastomeric member 80. Element 92 can generally be any well-known adhesive for securing the metallic members to an elastomeric member. For example, commercially available adhesives can secure titanium or stainless steel metals to body cavities. See the Handbook of Adhesives, Second Edition by Irving Skeist, copyrighted 1977 by Litton Educational Publishing, Inc., chapter 53 pertaining to Medical and Biological Adhesives, pages 818-835, hereby incorporated by reference.

The elastomeric members 80 can be comprised of any material stable within the body and can be stretched and relaxed repeatedly over a period of time. Suitable materials are commercially available elastomers, siloxanes and the like, such as, Silastic (trademark of Dow Corning Corporation for elastomeric materials comprising dimethyl siloxane, dimethyl vinyl—terminated and trimethylated silica) or stable synthetic rubber materials and the like. See for example Silastic MDX 4-4210 biomedical grade elastomer with catalyst, siloxane materials and the like. See also "Look what you can make out of silicones" by Barry Arkles CHEMTECH, 1983, 13, pp 542-555, hereby incorporated by reference. The reference lists numerous medical devices for the human body made from silicone polymers, such as siloxane.

The extendable elements 22 and 24 have outer elastomeric material 80 to which the metallic structure 50-50 E is attached. To facilitate the insertion of the rod into the body, a plastic C clip 84 is present between the central element 20 and the shoulder 119 (FIG. 8) of base 120 of piston 102. See FIGS. 3 and 5. Also, to further facilitate insertion of the rod, the elastomeric material 80 will have extra portion of elastomeric material 90 compressed together, as shown in the figures. The extra material is provided for separation of the cones in relaxed/flexible position.

During the insertion into the body, a suture 91, as shown in FIG. 3 and others, is wrapped around the rod components through slots 93 A and 93 B. The suture will assist in keeping the cones locked and rigid and assist in insertion of the rod into the body. The removal of the C clip and the suture will release the elastomeric member 80, thereby stretching the bulges 90. This can be seen by comparing FIGS. 3 and 5. The metallic cones 50-50E, as shown in FIG. 5, will have a space 51-51 F between them. The removal of the C clip and the suture will facilitate the rod to go from a rigid to a more flexible form, as is shown schematically in FIGS. 5 and 6, with the more flexible form shown in outline in FIG. 6 attached to FIG. 5.

The central portion 20 of the rod 11 has a sleeve 100 within which a piston 102 can move against the metallic member 50. As can be seen in comparing FIGS. 3 and 5, the piston 102 moves away from end 54 after the C clip and the suture are removed; see the arrow 104 in FIG. 5.

Under the movement of fluid in conduit 32, as shown in FIG. 8, by arrows 106, 107 and 108, the piston 102 moves toward the end 54, thereby extending the rod 11. Although not shown, the fluid moves by arrow 108 to move a piston towards end 52, which extends extensible portion 22. This therefore causes the rod 11 to go from a flexible position to an extended position reaching the extension schematically shown in FIG. 7. To illustrate this moment in the drawings, a gap 110 is shown between the central portion 20 and the base 120 of the piston 102.

To facilitate the action of the piston against the cones, as shown in FIG. 8, the piston head 140 is shaped to correspond with the base 142 of the cone 50. In addition, each of the cones 50 and 50 A-F are designed so that they substantially mate each other. For example, the top portion 150 of cone 50 will mate with the bottom portion 152 of cone 50 A. in a similar fashion, there will be heads and bottom portions for cones 50 A-50 F. Further, the shoulder 160 of the piston head 120 will be glued to the shoulder portion 162 of extendable element 24.

As shown in FIGS. 7 and 9, the hydraulic mechanism 29 is made up of activating apparatus 34, pumping mechanism 30 and conduit 32. While it is believed that any fluid can be passed from pumping mechanism 30 through conduit 32 into the rigid portion 20 of the rod 11, all that is required is that the fluid used have sufficient fluidity to move piston 102. Such fluids may be air, water based, such as, saline, and the like. Such pumps are well known in the medical device industry. For example, the SynchroMed (trademark of Medtronic) pumps are battery operated to introduce fluid materials into the human body. Such pumps can be readily converted to pump the fluid (such as saline and the like) from the cavity of the SynchroMed pump to the conduit 32, thereby causing pressure on the piston and moving it accordingly. Alternatively, similar pumps can be readily converted to pumping air, and likewise causing movement of the piston. It is to be appreciated that the movement of the fluid within applicants invention is to be considered a closed system. In other words, the fluid is designed to remain within the pumping and rod mechanisms. However, as is currently performed with the SynchroMed pump which it delivers drugs to a patient, the pump utilized in applicant's invention can be replenished with a water based fluid, should leakage occur in the desired closed system described herein.

The activating apparatus 34 is the mechanism that causes the pump 30 to be activated. In the case of the SynchroMed pump, the activating apparatus is the battery and electronic modules stored within the pump apparatus. Alternatively, electronic apparatus may be utilized such as microwave devices or radio wave devices, which can activate a motor, such as, those routinely used for opening and closing garage doors, locking and unlocking vehicles and the like. Such devices can activate a pump to cause the fluid to flow against the piston.

As shown in FIGS. 7 and 9 (which is at 90° to FIG. 7, and comparable to FIG. 2), the garment 120 is put on by the patient. When the garment is put on the patient, it's activating apparatus 122 (shown as 122 A in outline on FIG. 7) is in alignment with the activating apparatus 34 of the hydraulic mechanism 30. When the activating apparatus 122 is turned on, electronic or magnetic waves and the like 134 are implemented thereby activating the apparatus 34 and causing the pump 30 to be activated. This in turn causes movement of the fluid through the conduit 32 into solid member 20, which then causes movement of the piston 102. The rod 11 is thereby extended.

It is to be appreciated that the activating apparatus 122 can be arranged so that there is an on or off mechanism 124, which in turn can activate the appropriate electromagnetic or electronic device 126. The electronic device causes the electromagnetic or electronic waves 134 to activate the apparatus 34.

An alternative embodiment is shown in FIGS. 10 and 11. A pressure relief mechanism 130 is shown to be interconnected with the cones 50-50 E. It may be desirable to modify the rod 11, to permit a pressure release through channels 132 and 132 A-F and the cones 50-50 E. The pressure relief mechanism 130 may be a bladder that can be filled with the fluid as shown in FIG. 11 by expanding bladder 134.

Another alternative embodiment is shown in FIG. 12. In FIG. 12, a separate piston is not used as is utilized in the previous FIGS. 3, 5 and 8. In the embodiment of FIG. 12, the fluid flows through conduit 32 and moves the cones 50A-50 B thereby causing the rod 11 to be expanded. After in insertion of the rod into the patient, the C clip 84 will be removed, thereby closing gap 35, as shown in FIG. 12. In this embodiment, the conduit 32 is shown with extension 33 within the interior of a slidable member 180. The top portion 182 of the slidable member 180 is shaped like cone member 50 of FIGS. 3, 5 and 8. In this fashion, top portion 182 will engage cones 50 A-B as described previously. To permit the fluid to move slidable member 180, the fluid will move through conduit 190 and contact the interior 192 of slidable member 180. The action of the slidable member against the cones will thereby extend the rod via extendable portion 24.

While the forms of the invention herein disclosed constitute presently preferred embodiments, many others are possible. It is not intended herein to mention all of the possible equivalent forms or ramifications of the invention. The rod may also be used to perform compression across the spine as well as distraction. It is understood that the terms used herein are merely descriptive rather than limiting and that various changes may be made without departing from the spirit or the scope of the invention. For example the types of metal, elastomeric material, activating mechanisms, types of garment, composition of the rod and the like can all be varied based on the skill of one in the art for the various compositions and activating mechanisms as described herein.

The invention claimed is:

1. An apparatus for treatment of a body having a skeletal curvature comprising:
    a rod capable of being attached to at least two vertebrae of the spine;
    which rod, under fluid pressure, moves from a first position to an extended position;
    which extended position straightens the two vertebrae;
    wherein the rod is more flexible in the first position than in the extended position; and
    a hydraulic mechanism, in fluid communication with the rod,
    which moves the rod from the first position to the extended position,
    wherein the rod and hydraulic mechanism are capable of being inserted within the body having a skeletal curvature
    wherein the rod includes a central portion and a segment attached to the central portion, the segment including:
        a plurality of cones capable of fitting one juxtaposed to the other;
        an elastomeric member fixedly attached to each of the plurality of cones;
        wherein the elastomeric member comprises an elastomeric material;
        wherein the plurality of cones are configured to move together to lock when the rod is under fluid pressure such that the segment moves to the extended position and the segment is rigid; and
        wherein the plurality of cones are configured to move apart from one another when the rod is not under fluid pressure such that the segment moves to the first position and the segment is flexible.

2. The apparatus of claim 1 further comprising a garment, capable of being worn external to the body in which the rod and hydraulic mechanism are inserted, wherein the garment comprises an activating mechanism to cause the hydraulic mechanism to move the rod from the first position to the extended position.

3. The apparatus of claim 2 wherein when the garment is not worn, the fluid pressure is relieved, thereby causing the rod to be more flexible than in the extended position.

4. The apparatus of claim 1 wherein the elastomeric material is a siloxane material.

5. The apparatus of claim 1 wherein the plurality of cones comprise a metallic material.

6. The apparatus of claim 5 wherein the metallic material comprises titanium or stainless steel.

7. The apparatus of claim 1 wherein the hydraulic mechanism utilizes a fluid comprising an aqueous-based material.

8. A method of moving vertebrae in a spine having a curvature comprising providing the apparatus of claim 1; and causing the fluid to move in the hydraulic mechanism thereby moving the vertebrae.

9. The method of claim 8 wherein the apparatus further comprises a garment, capable of being worn external to the body in which the rod and hydraulic mechanism are inserted, wherein the garment comprises an activating mechanism to cause the hydraulic mechanism to move the rod from the first position to the extended position.

10. The method of claim 9 further comprising removing the garment, thereby relieving the fluid pressure, thereby causing the rod to be more flexible than in the extended position.

11. The method of claim 8 wherein the body having the curvature does not have the vertebrae fused.

12. A flexible rod capable of being attached to vertebrae of the spine comprising:
    a first end capable of being attached to one vertebra and a second end, separated from the first end and capable of attaching to a separate second vertebra,
    which rod, under fluid pressure, moves from a first position to an extended position, which extended position straightens the vertebrae; and
    a segment which defines a chamber located between the ends and within which chamber is located a plurality of cones;
    an elastomeric member fixedly attached to each of the plurality of cones;
    wherein the elastomeric member comprises an elastomeric material;
    under fluid pressure the plurality of cones move together to engage each other to make the rod less flexible in the extended position; and
    wherein the plurality of cones move apart from one another when the rod is not under fluid pressure such that the segment, including the plurality of cones and the elastomeric member, is flexible in the first position.

13. The apparatus of claim 12 further comprising a garment, capable of being worn external to a body in which the rod is inserted, wherein the garment comprises an activating mechanism to cause the fluid to move the cones thereby moving the rod from the first position to the extended position.

14. The apparatus of claim 13 wherein when the garment is not worn, the fluid pressure is relieved, thereby causing the rod to be more flexible than in the extended position.

15. The apparatus of claim 12 wherein the rod further comprises a central element, the segment attached thereto, the central element and segment capable of being extended from an initial position to an extended position.

16. The apparatus of claim 12 wherein the elastomeric material is a siloxane material.

17. The apparatus of claim 12 wherein the plurality of cones are capable of fitting one juxtaposed to the other, thereby extending the rod when under fluid pressure in the extended position.

18. The apparatus of claim 17 wherein the plurality of cones comprise a metallic material.

19. The apparatus of claim 18 wherein the metallic material is comprised of titanium or stainless steel.

20. The apparatus of claim 12 wherein the fluid comprises an aqueous-based material.

21. A method of moving vertebrae in a body having a skeletal curvature comprising providing the apparatus of claim 12; and causing fluid to move in the chamber to move the cones, thereby moving the vertebrae.

22. The method of claim 21 wherein the apparatus further comprises a garment, capable of being worn external to the body in which the rod is inserted, wherein the garment comprises an activating mechanism to cause the fluid to move the cones, thereby moving the rod from the first position to the extended position.

23. The method of claim 22 further comprising removing the garment, thereby relieving the fluid pressure, thereby causing the rod to be more flexible than in the extended position.

24. The method of claim 21 wherein the body having the curvature does not have the vertebrae fused.

25. An apparatus for treatment of a body having a skeletal curvature comprising:

a rod capable of being attached to at least two vertebrae of the spine;

which rod, under fluid pressure moves from a first position to an extended position, which extended position straightens the two vertebrae; and a hydraulic mechanism, in fluid communication with the rod, which moves the rod from the first position to the extended position, wherein the rod and hydraulic mechanism are capable of being inserted within the body having a skeletal curvature, further comprising a garment, capable of being worn external to the body in which the rod and hydraulic mechanism are inserted, wherein the garment comprises an activating mechanism to cause the hydraulic mechanism to move the rod from the first position to the extended position, wherein the rod further comprises a fixed central element and a segment, attached thereto, capable of being extended from an initial position to an extended position, when the rod is under fluid pressure, which segment capable of being extended includes an elastomeric member comprised of an elastomeric material and the segment further comprises a chamber in which there is a plurality of metallic cones capable of fitting one juxtaposed to the other thereby extending the rod, wherein each of the plurality of metallic cones are fixedly attached to the elastomeric member;

wherein the rod is more flexible in the first position than in the extended position.

26. A method of moving vertebrae in a spine having a curvature comprising providing the apparatus of claim 25; and causing fluid to move in the hydraulic mechanism thereby moving the vertebrae.

\* \* \* \* \*